(12) United States Patent
Jeong

(10) Patent No.: US 10,646,162 B2
(45) Date of Patent: May 12, 2020

(54) WEARABLE DEVICE CAPABLE OF HAVING SENSOR FOR DETECTING BIOLOGICAL SIGNAL ATTACHED THERETO OR DETACHED THEREFROM AND METHOD OF CONTROLLING THE WEARABLE DEVICE

(71) Applicant: SAMSUNG ELECTRONICS CO., LTD., Suwon-si (KR)

(72) Inventor: Sanghwa Jeong, Yongin-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 35 days.

(21) Appl. No.: 15/979,912

(22) Filed: May 15, 2018

(65) Prior Publication Data

US 2018/0256104 A1    Sep. 13, 2018

Related U.S. Application Data

(62) Division of application No. 14/719,949, filed on May 22, 2015, now Pat. No. 9,993,200.

(30) Foreign Application Priority Data

Oct. 8, 2014  (KR) .......................... 10-2014-0135958

(51) Int. Cl.
  *A61B 5/00*  (2006.01)
  *G06F 1/16*  (2006.01)
  (Continued)

(52) U.S. Cl.
  CPC ............ *A61B 5/681* (2013.01); *A61B 5/0015* (2013.01); *G04G 21/02* (2013.01); *G06F 1/163* (2013.01);
  (Continued)

(58) Field of Classification Search
  CPC ..... A61B 5/681; A61B 5/0015; A61B 5/0059; A61B 5/01; A61B 5/02416; A61B 5/0261;
  (Continued)

(56) References Cited

U.S. PATENT DOCUMENTS 5,529,755 A * 6/1996 Higashio ............ A61B 5/14532
                                                    422/82.09
8,944,958 B1 * 2/2015 Brumback .............. G06F 19/00
                                                    482/8

(Continued)

FOREIGN PATENT DOCUMENTS

KR   10-2010-0062125 A    6/2010
KR   10-2013-0024468 A    3/2013
WO       2012/172487 A1  12/2012

OTHER PUBLICATIONS

Communication dated Apr. 21, 2016, from the European Patent Office in counterpart European Application No. 15176116.0.

(Continued)

*Primary Examiner* — Emily C Terrell
*Assistant Examiner* — Rufus C Point
(74) *Attorney, Agent, or Firm* — Sughrue Mion, PLLC

(57) ABSTRACT

Provided are a wearable device capable of having a sensor for detecting a biological signal attached thereto or detached therefrom, and a method of controlling the wearable device. The wearable device includes: a strap part configured to be worn on a body part of a user; a first interface configured to accommodate a detachable sensor and receive a biological signal from the detachable sensor in response to the detachable sensor being connected to the wearable device through the first interface; and a main body configured to process the biological signal.

13 Claims, 10 Drawing Sheets

(51) Int. Cl.
| | |
|---|---|
| *G04G 21/02* | (2010.01) |
| *A61B 5/01* | (2006.01) |
| *A61B 5/024* | (2006.01) |
| *A61B 5/026* | (2006.01) |
| *A61B 5/053* | (2006.01) |
| *A61B 5/145* | (2006.01) |
| *A61B 5/1455* | (2006.01) |

(52) U.S. Cl.
CPC .......... *G06F 1/1684* (2013.01); *G06F 1/1694* (2013.01); *G06F 1/1698* (2013.01); *A61B 5/0059* (2013.01); *A61B 5/01* (2013.01); *A61B 5/0261* (2013.01); *A61B 5/02416* (2013.01); *A61B 5/0531* (2013.01); *A61B 5/1455* (2013.01); *A61B 5/14532* (2013.01); *A61B 5/14546* (2013.01); *A61B 5/4266* (2013.01); *A61B 5/4872* (2013.01); *A61B 5/742* (2013.01); *A61B 5/745* (2013.01); *A61B 5/7475* (2013.01); *A61B 2560/0443* (2013.01); *A61B 2560/0456* (2013.01); *A61B 2562/227* (2013.01)

(58) Field of Classification Search
CPC .............. A61B 5/0531; A61B 5/14532; A61B 5/14546; A61B 5/1455; A61B 5/4266; A61B 5/4872; A61B 5/742; A61B 5/745; A61B 5/7475; A61B 2560/0443; A61B 2560/0456; A61B 2562/227; G04G 21/02; G06F 1/1694; G06F 1/1698
See application file for complete search history.

(56) References Cited

U.S. PATENT DOCUMENTS

| | | | |
|---|---|---|---|
| 9,615,794 B2 * | 4/2017 | Kaskoun | A61B 5/6833 |
| 10,049,595 B1 * | 8/2018 | Chuang | G09B 19/00 |
| 10,204,292 B2 * | 2/2019 | Choi | G06K 9/6293 |
| 2001/0043514 A1 | 11/2001 | Kita | |
| 2007/0016381 A1 * | 1/2007 | Kamath | A61B 5/14532 702/19 |
| 2009/0143689 A1 | 6/2009 | Berry et al. | |
| 2009/0216499 A1 * | 8/2009 | Tobola | A61B 5/02416 702/190 |
| 2009/0299157 A1 * | 12/2009 | Telfort | A61B 5/14551 600/301 |
| 2009/0322513 A1 | 12/2009 | Hwang et al. | |
| 2010/0030039 A1 * | 2/2010 | Lamego | A61B 5/6829 600/310 |
| 2010/0298651 A1 * | 11/2010 | Moon | A61B 5/0002 600/301 |
| 2010/0298687 A1 * | 11/2010 | Yoo | A61B 5/0006 600/391 |
| 2010/0311544 A1 | 12/2010 | Robinette et al. | |
| 2011/0257496 A1 | 10/2011 | Terashima et al. | |
| 2012/0253147 A1 * | 10/2012 | Huiku | A61B 5/14551 600/310 |
| 2013/0168573 A1 * | 7/2013 | Yamanaka | G01N 21/6456 250/459.1 |
| 2013/0211204 A1 | 8/2013 | Caduff et al. | |
| 2014/0073486 A1 | 3/2014 | Ahmed et al. | |
| 2014/0275850 A1 * | 9/2014 | Venkatraman | A61B 5/4812 600/301 |
| 2014/0275852 A1 | 9/2014 | Hong et al. | |
| 2014/0378791 A1 * | 12/2014 | DeHennis | A61B 5/0015 600/310 |
| 2015/0148623 A1 * | 5/2015 | Benaron | A61B 5/0059 600/306 |
| 2015/0150505 A1 * | 6/2015 | Kaskoun | A61B 5/6833 600/300 |
| 2015/0157219 A1 * | 6/2015 | Lee | A61B 5/0531 600/393 |
| 2016/0100758 A1 * | 4/2016 | Jeong | G06F 1/1684 340/870.07 |
| 2016/0174840 A1 * | 6/2016 | Udoh | A61B 5/0022 600/595 |
| 2018/0014781 A1 * | 1/2018 | Clavelle | A61B 5/02422 |
| 2018/0220956 A1 * | 8/2018 | Kuhar | A61B 5/4557 |
| 2018/0360373 A1 * | 12/2018 | Aarts | A61B 5/0059 |
| 2019/0046121 A1 * | 2/2019 | Khachaturian | G16H 30/40 |

OTHER PUBLICATIONS

Office Action dated May 1, 2017 by the U.S. Patent and Trademark Office in parent U.S. Appl. No. 14/719,949.
Office Action dated Oct. 23, 2017 by the U.S. Patent and Trademark Office in parent U.S. Appl. No. 14/719,949.
Notice of Allowance dated Feb. 12, 2018 by the U.S. Patent and Trademark Office in parent U.S. Appl. No. 14/719,949.

* cited by examiner

WEARABLE DEVICE CAPABLE OF HAVING SENSOR FOR DETECTING BIOLOGICAL SIGNAL ATTACHED THERETO OR DETACHED THEREFROM AND METHOD OF CONTROLLING THE WEARABLE DEVICE

CROSS-REFERENCE TO RELATED APPLICATION

This is a divisional application of U.S. application Ser. No. 14/719,949 filed on May 22, 2015, which claims priority from Korean Patent Application No. 10-2014-0135958, filed on Oct. 8, 2014 in the Korean Intellectual Property Office, the disclosures of which are incorporated herein in their entirety by reference.

BACKGROUND

1. Field

Exemplary apparatuses and methods relate to a wearable device capable of having a sensor for detecting a biological signal attached thereto or detached therefrom and a method of controlling the wearable device.

2. Description of the Related Art

Due to developments in science and technologies, mobile devices, such as smartphones, are widely used. Also, since health and disease awareness has become more prominent, a sensor for detecting a biological signal is being developed. The biological signal may be detected by a sensor which is embedded in a mobile device and is driven by using the mobile device.

SUMMARY

One or more exemplary embodiments provide a wearable device capable of having a sensor for detecting a biological signal easily attached thereto or detached therefrom, and a method of controlling the wearable device.

According to an aspect of an exemplary embodiment, there is provided a wearable device including: a strap part configured to be worn on a body part of a user; a first interface disposed at a predetermined position of the strap part and configured to accommodate a detachable sensor and receive a biological signal from the sensor in response to the sensor being connected to the wearable device through the first interface; and a main body configured to process the biological signal.

The strap part may include a wiring configured to connect the first interface and the main body.

The strap part and the first interface may be formed of a flexible material.

The first interface may include a plurality of sub-interfaces to which different types of sensors are attached.

The wearable device may further include a second interface that is disposed in the main body and configured to receive the biological signal from the sensor in response to the sensor being attached to the wearable device.

A predetermined portion of an exterior case of the main body that contacts the body part may be transparent.

The predetermined portion of the exterior case of the main body that contacts the body part may open or may close according to whether the second interface is attached to the sensor.

The second interface may include a plurality of sub-interfaces to which different types of sensors are attached.

According to an aspect of another exemplary embodiment, there is provided a wearable device including: an interface configured to receive, from a detachable sensor that is attached to the wearable device, information about a method of detecting a biological signal detected by the attached sensor; and a controller configured to recognize a type of the attached detachable sensor based on the information about the method of detecting the biological signal, and generate biological information corresponding to the type of the recognized sensor, based on the biological signal.

The information about the method of detecting the biological signal may include information about a wavelength and an intensity of light that is radiated by the attached detachable sensor.

The wearable device may further include an output unit configured to output the biological information, display one or more functions of the recognized detachable sensor on a user interface of the wearable device, and receive an input of selecting a user-desired function from among the one or more functions. The interface may receive, from the attached detachable sensor, a biological signal that corresponds to the user-desired function.

The wearable device may further include an output unit configured to display one or more functions of the recognized sensor on a user interface of the wearable device, receive an input for selecting a user-desired function from among the one or more functions, and output biological information that corresponds to the user-desired function.

The wearable device may further include an output unit configured to output biological information and output information about changes over time in the biological information during a predetermined period.

The interface may include a plurality of sub-interfaces to which different types of a plurality of sensors are attached. The plurality of sensors include the detachable sensor and the controller may be further configured to recognize at least one from among the plurality of sensors.

According to an aspect of another exemplary embodiment, there is provided a method of a wearable device including: receiving information about a method of detecting a biological signal from a detachable sensor that is attached to the wearable device; recognizing a type of the attached detachable sensor, based on the information about the method of detecting the biological signal; receiving the biological signal from the attached sensor in response to the biological signal being detected by the attached detachable sensor; and generating, based on the biological signal, biological information that corresponds to the type of the recognized detachable sensor.

The information about the method of detecting the biological signal may include information about a wavelength and an intensity of light that is radiated by the attached sensor.

The receiving the biological signal may include operations of displaying one or more functions of the recognized detachable sensor on a user interface of the wearable device; receiving an input of selecting a user-desired function from among the one or more functions; and receiving, from the attached detachable sensor, a biological signal that corresponds to the user-desired function.

The method of the wearable device may further include displaying one or more functions of the recognized detachable sensor on a user interface of the wearable device; receiving an input for selecting a user-desired function from among the one or more functions; and outputting the biological information that corresponds to the user-desired function.

The method of the wearable device may further include outputting the biological information and outputting information about changes in the biological information over time during a predetermined period.

The receiving the information about the method of detecting the biological signal may include an operation of receiving the information about the method of detecting the biological signal from each of different-type sensors that are attached to the wearable device. The different-type sensors may include the detachable sensor.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
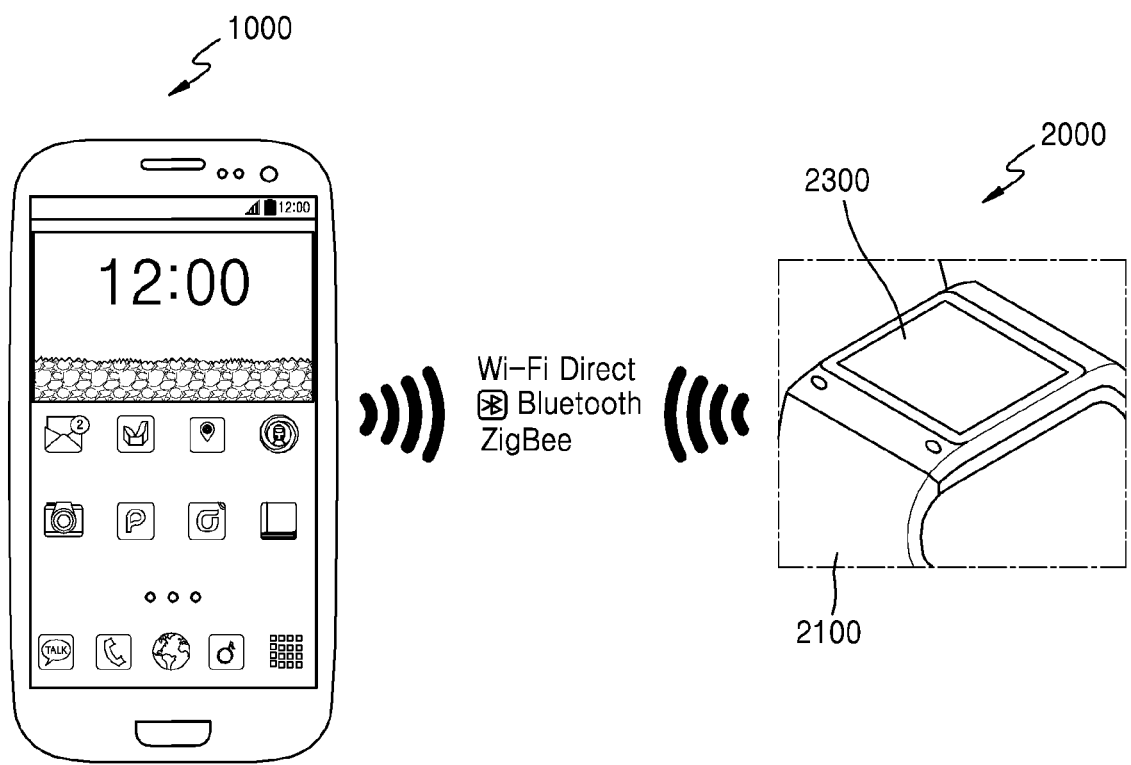
FIG. 1 illustrates a communication environment of a wearable device.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Throughout the specification, it will be further understood that the terms "configured", "configuring", "formed", and/or "forming" and "comprises", "comprising,", "includes" and/or "including", when used herein, specify the presence of stated components, steps, or operations, but do not preclude the absence of one or more of the components, the steps, or the operations or the addition of one or more other components, steps, or operations.

While such terms as "first," "second," etc., may be used to describe various components, such components must not be limited to the above terms. The above terms are used only to distinguish one component from another.

One or more exemplary embodiments are related to a wearable device to or from which a sensor for detecting a biological signal is attached or detached, and a method of controlling the wearable device. In the following description, functions or constructions that are well-known to one of ordinary skill in the art will not be described in detail.

As used herein, the term "and/or" includes any and all combinations of one or more of the associated listed items. Expressions such as "at least one of," when preceding a list of elements, modify the entire list of elements and do not modify the individual elements of the list.

FIG. 1 illustrations a communication environment of a wearable device 2000.

As illustrated in FIG. 1, a mobile device 1000 and the wearable device 2000 may exchange data wirelessly, for example, by using a short-distance wireless communication. Here, the short-distance wireless communication such as Wi-Fi direct, Bluetooth, or ZigBee may consume only a small amount of power.

The wearable device 2000 may use the mobile device 1000 to receive data from a remote device or to transmit data to the remote device. For example, the wearable device 2000 may transmit data to the remote device by transmitting the data to the mobile device 1000 by using the short-distance wireless communication and then the mobile device 1000 re-transmits the data to the remote device.

The wearable device 2000 may indicate any device that may be worn on a body part of a user. To do so, the wearable device 2000 may be divided into a strap part 2100 and a main body 2300. The strap part 2100 is a configuration of the wearable device 2000 that has a form allowing the wearable device 2000 to be worn on the body part of the user, and the main body 2300 is another configuration of the wearable device 2000 that performs a characteristic function of the wearable device 2000.

The user may attach a sensor 3000 for detecting a biological signal to the wearable device 2000 or detach the sensor 3000 from the wearable device 2000. In other words, the user may insert the sensor 3000 into the wearable device 2000, remove the inserted sensor 3000 from the wearable device 2000, and replace the removed sensor 3000 with another sensor. A type of the sensor 3000 may vary according to a detection-target biological signal, or one sensor 3000 may detect various biological signals.

The body part of the user who wears the wearable device 2000 may indicate a part of a body from which the detection-target biological signal is detected. For example, the body part of the user who wears the wearable device 2000 may include a wrist, an ankle, a head, a neck, an arm, or the like.

According to a type of the detection-target biological signal, a type and form of the sensor 3000 may vary, and a position of the wearable device 2000 to which the sensor 3000 is to be attached may vary. Hereinafter, the position of the wearable device 2000 to which the sensor 3000 is to be attached, an interfacing method of the wearable device 2000, and a method of recognizing a type of the sensor 3000 attached to the wearable device 2000, the method being performed by the wearable device 2000, will be described.

Figure 2:
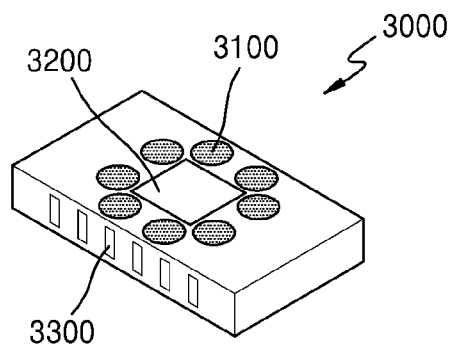
FIG. 2 illustrates a sensor that is attachable to and detachable from the wearable device, according to an exemplary embodiment.

FIG. 2 illustrates the sensor 3000 that is attachable to or is detachable from the wearable device 2000, according to an exemplary embodiment.

FIG. 2 illustrates an example of the sensor 3000 that is attachable to or detachable from the wearable device 2000. According to a method of detecting a biological signal, a form or a configuration of the sensor 3000 may vary. In one example, an electrode of the sensor 3000 may be in contact with a body part of a user that is a detection target of the biological signal, and impedance of the user may be measured. In another example, light may be radiated to the body part that is the detection target of the biological signal, and light that is reflected from the body part in response to the radiated light may be detected. In another example, ultrasound may be radiated to the body part that is the detection target of the biological signal, and ultrasound that is reflected from the body part in response to the radiated ultrasound may be detected. Hereinafter, for convenience of description, it is assumed that the sensor 3000 detects the biological signal by using light.

As illustrated in FIG. 2, the sensor 3000 may include an irradiator 3100, a detector 3200, and a sensor interface 3300. If the sensor 3000 of FIG. 2 is a photo-sensor that uses light, the irradiator 3100 may have a light source and may irradiate the body part using the light source. The detector 3200 may detect light that is reflected from a biological tissue and may include a photoelectric conversion device such as a photodiode. The irradiator 3100 and the detector 3200 may be disposed on a same surface of the sensor 3000.

The sensor interface 3300 may be a part that connects the sensor 3000 and the wearable device 2000 when the sensor 3000 is attached to the wearable device 2000, and may function as a path along which the sensor 3000 and the wearable device 2000 exchange data. The sensor 3000 that is attached to the wearable device 2000 may transmit information about a method of detecting a biological signal (hereinafter, referred to as "biological signal detection information") and the biological signal that is detected by the attached sensor 3000 to the wearable device 2000. As illustrated in FIG. 2, the sensor interface 3300 may be disposed on a surface that is different from the surface on which the irradiator 3100 and the detector 3200 are disposed.

The sensor interface 3300 may include a plurality of electrodes that may be electrically connected to the wearable device 2000. For example, the sensor interface 3300 may include a ground electrode, an electrode for sensing attachment or detachment of the sensor 3000, an electrode for checking a power supply to the sensor 3000, an electrode for transmitting data to the wearable device 2000, an electrode for receiving data from the wearable device 2000, a clock electrode for receiving an input of a clock signal, etc.

According to relative positions of the irradiator 3100, the detector 3200, and the sensor interface 3300, a position of the wearable device 2000 to which the sensor 3000 is to be attached may vary. Hereinafter, a first interface 2120 of the wearable device 2000 to which the sensor 3000 may be attached is described with reference to FIG. 3A.

Figure 3A:
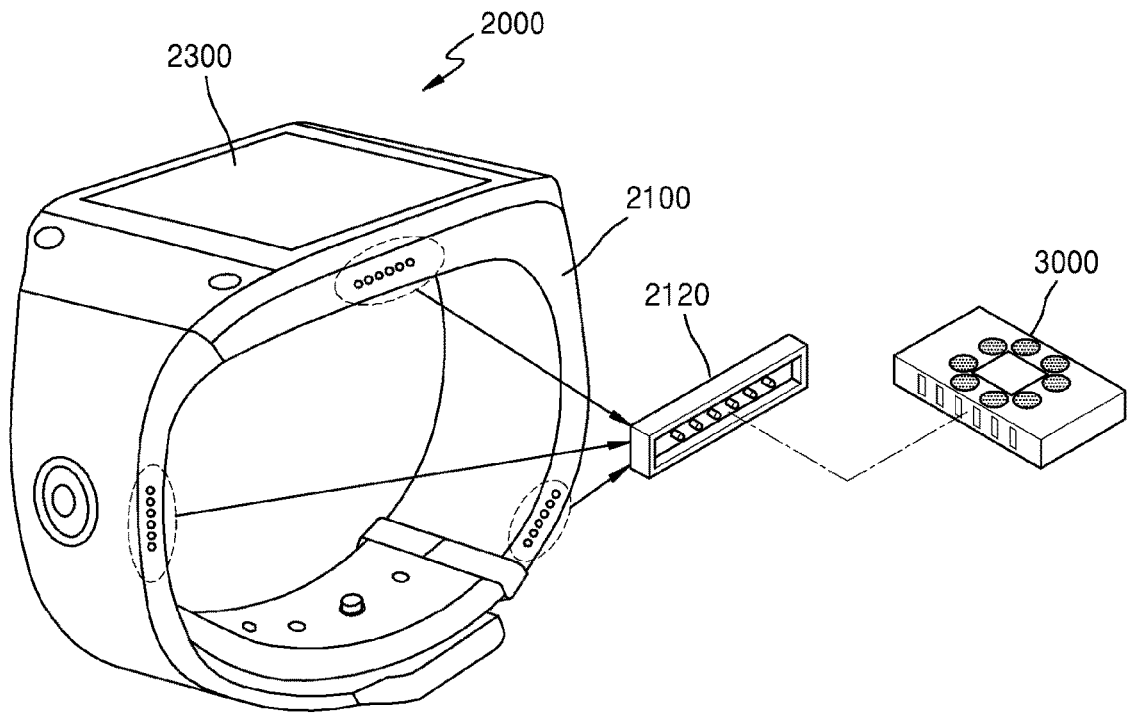
FIG. 3A illustrates a first interface of the wearable device according to an exemplary embodiment.

FIG. 3A illustrates the first interface 2120 of the wearable device 2000, according to an exemplary embodiment.

Referring to FIG. 3A, the wearable device 2000 may include the strap part 2100 that allows the wearable device 2000 to be worn on a body part of a user, and the main body 2300 that is connected to the strap part 2100. As illustrated in FIG. 3A, the wearable device 2000 may be a watch-type wearable device but is not limited thereto and may have one of various forms including a necklace-type wearable device, a bracelet-type wearable device, a band-type wearable device, a hat-type wearable device, etc.

The strap part 2100 and the main body 2300 may be separable or may have one body that is not separated.

The first interface 2120 may be disposed at a predetermined position of the strap part 2100 of the wearable device 2000 and configured to accommodate the sensor 3000 which is attachable and detachable. The first interface 2120 may receive biological signal detection information from the sensor 3000 that is attached to the wearable device 2000. Also, the first interface 2120 may receive a biological signal that is detected by the attached sensor 3000. Here, in a case of the photo-sensor such as the sensor 3000 shown in FIG. 2, the biological signal detection information may include information about a wavelength and intensity of light that is radiated by the sensor 3000 attached to the wearable device 2000.

As illustrated in FIG. 3A, the predetermined position of the strap part 2100 of the wearable device 2000 at which the first interface 2120 may be disposed may be a random position on a side surface of the strap part 2100 when a user wears the wearable device 2000. Also, a plurality of the first interfaces 2120 may simultaneously exist at several positions of the strap part 2100.

Referring to FIG. 3A, the sensor 3000 may be attached or detached even when the user wears the wearable device 2000. Also, when the sensor 3000 malfunctions or is broken, the user may detach the sensor 3000 from the wearable device 2000 and may repair only the sensor 3000.

As illustrated in FIG. 3A, when the wearable device 2000 is a watch-type wearable device, the strap part 2100 and the first interface 2120 may be flexible but one or more exemplary embodiments are not limited thereto.

Referring to FIG. 3A, the first interface 2120 may have a plurality of pins that may be electrically connected to the sensor 3000. For example, the first interface 2120 may have a pin for connection to ground, a sensing pin for sensing attachment or detachment of the sensor 3000, a power pin for checking a power supply to the attached sensor 3000, a transmitting pin for transmitting data to the attached sensor 3000, a receiving pin for receiving data from the attached sensor 3000, a clock pin for receiving a clock signal, or the like.

Further, the first interface 2120 and the sensor 3000 may have a universal serial bus (USB) connector type such as type A, type B, Mini-A, Mini-B, Micro-A, Micro-B, or Micro-AB. In addition, although FIG. 3A illustrates the first interface 2120 as a male connector (also referred to as a plug) and the sensor as having a female connector (also referred to as a receptacle or a port), one or more other exemplary embodiments are limited thereto. For example, the first interface 2120 may correspond to a USB Type A female connector and the sensor 3000 may have a corresponding USB Type A male connector.

When the sensor 3000 is attached to the first interface 2120 of the wearable device 2000, the plurality of pins of the first interface 2120 may contact the electrodes of the sensor interface 3300 of the sensor 3000, respectively, and connect the wearable device 2000 and the sensor 3000, As a result, the wearable device 2000 and the attached sensor 3000 are able to communication to exchange data.

Figure 3B:
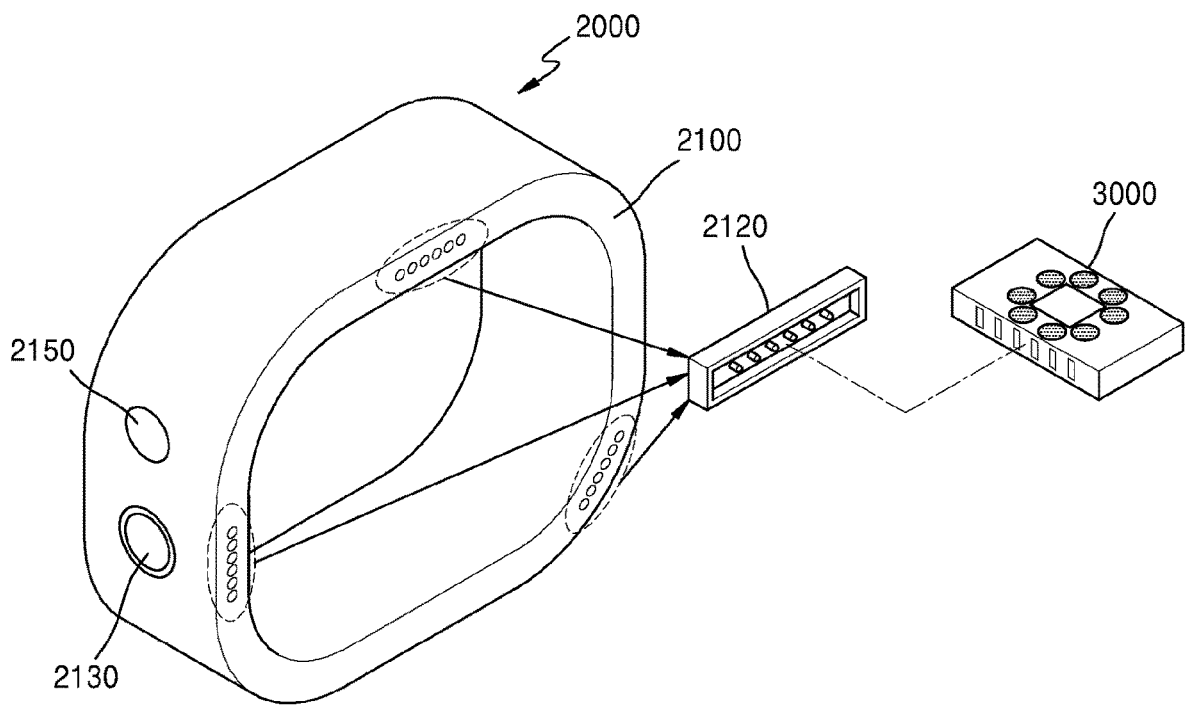
FIG. 3B illustrates a first interface of the wearable device according to another exemplary embodiment.

FIG. 3B illustrates a wearable device 2000 including a strap part 2100 and a first interface 2120 disposed at the start part 2100, according to another exemplary embodiment.

As shown in FIG. 3B, the wearable device 2000 does not include the main body 2300 of FIG. 3A to provide extended battery life. Instead, the wearable device 2000 of FIG. 3B may include an indicator 2130 such as a vibrator motor or a multi-color LED. The indicator 2130 may notify a user of biological information (e.g., body fat level, blood sugar level, temperature, sweat, and creatinine level) detected by the sensor 300 when the sensor 300 is inserted into the first interface 2120 and in contact with the user. More specifically, the indicator 2130 may push notifications corresponding the detected biological information via the multi-color LED and/or the vibrator motor. Further, the wearable device 2000 may include a communication unit 2150 that transmits the biological information to an external device (e.g., the mobile device 1000 of FIG. 1).

Figure 4:
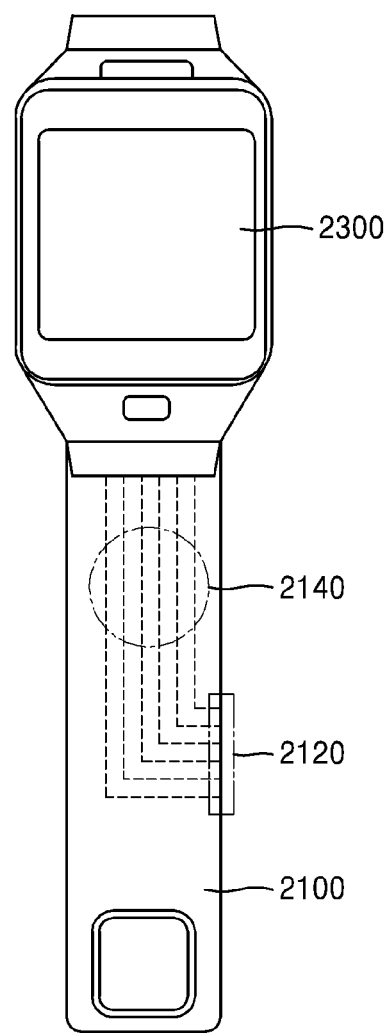
FIG. 4 illustrates a strap part of the wearable device of FIG. 3A, according to an exemplary embodiment.

FIG. 4 illustrates the strap part 2100 of the wearable device 2000, according to an exemplary embodiment.

Referring to FIG. 4, the strap part 2100 may have a wiring 2140 that connects the main body 2300 and the first interface 2120. A shape, a length, and an array of the wiring 2140 may vary according to a location of the first interface 2120.

Since the strap part 2100 and the first interface 2120 may be flexible, when a form of the strap part 2100 is changed, a form of the wiring 2140 that is arranged at the strap part 2100 may be changed according to the changed form of the strap part 2100.

If a plurality of the first interfaces 2120 exist, the strap part 2100 may include a plurality of the wirings 2140 that correspond to the plurality of the first interfaces 2120, respectively.

Figure 5:
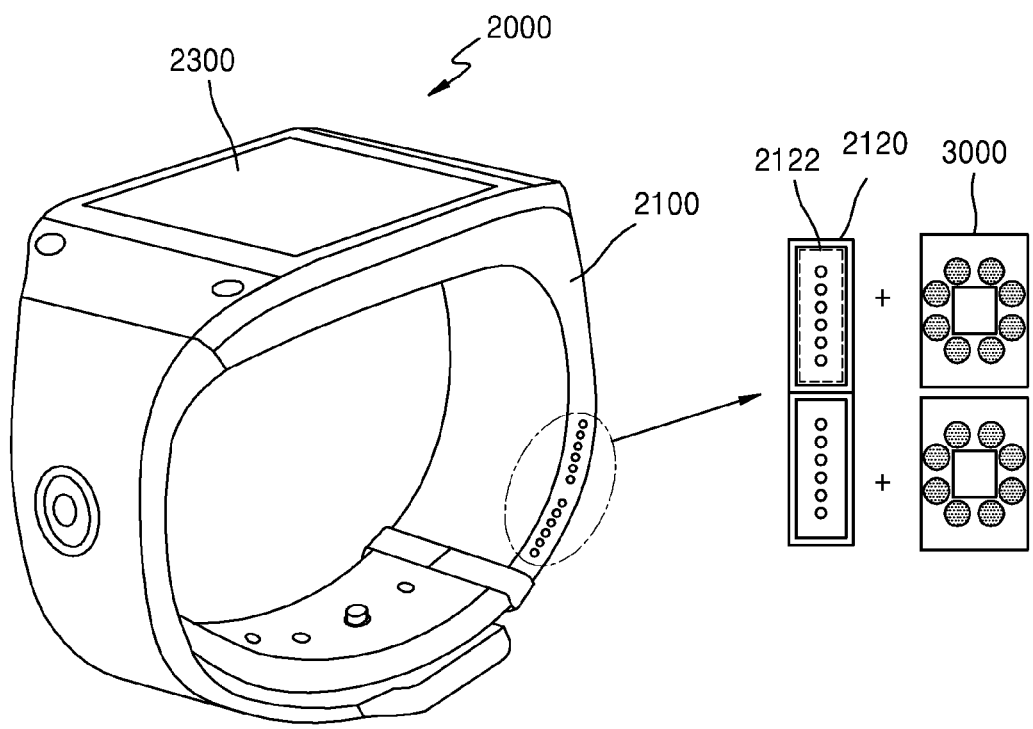
FIG. 5 illustrates a form of the first interface of FIGS. 3A and 3B, according to another exemplary embodiment.

FIG. 5 illustrates a form of the first interface 2120 of the wearable device 2000, according to another exemplary embodiment.

Referring to FIG. 5, the first interface 2120 may include a plurality of sub-interfaces 2122 to which the sensors 3000 may be attached.

For example, if a type of the sensor 3000 varies according to a type of a biological signal, a user of the wearable device 2000 has to attach different types of the sensors 3000 to the wearable device 2000. Alternatively, if it is required to simultaneously detect biological signals from several body parts of the user, the user of the wearable device 2000 may have to attach one type of the sensors 3000 to the wearable device 2000. Thus, the user may attach different types or one type of the sensors 3000 to the first interface 2120 of the wearable device 2000 that includes the sub-interfaces 2122.

The sensors 3000 may be simultaneously attached to the sub-interfaces 2122. Alternatively, if there is no need for the sensors 3000 to correspond to the number of the sub-interfaces 2122 included in the first interface 2120, the sensors 3000 may be attached to only some of the sub-interfaces 2122.

Figure 6:
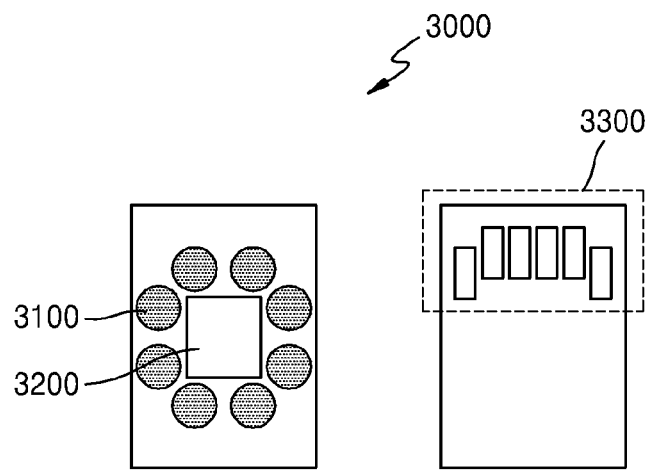
FIG. 6 illustrates the sensor that is attachable to and detachable from a wearable device, according to another exemplary embodiment.

FIG. 6 illustrates the sensor 3000 that is attachable to or detachable from the wearable device 2000, according to another exemplary embodiment.

As described above with reference to FIG. 2, according to a method of detecting a biological signal, a form or a configuration of the sensor 3000 that is attachable to or detachable from the wearable device 2000 may vary. For convenience of description, it is assumed that the sensor 3000 detects a biological signal by using light.

As illustrated in FIG. 6, the sensor 3000 may be manufactured in the form of a chip such as a memory card. In other words, the sensor 3000 may be manufactured to be inserted into and to be mounted at a slot that is formed at a predetermined position of the wearable device 2000.

As illustrated in FIG. 6, the sensor 3000 may include an irradiator 3100, a detector 3200, and a sensor interface 3300. If the sensor 3000 of FIG. 6 is a photo-sensor that uses light, the irradiator 3100 may have a light source and may radiate the light to a body part. The detector 3200 may detect light that is reflected from a biological tissue and may include a photoelectric conversion device such as a photodiode. The irradiator 3100 and the detector 3200 may be disposed on a same surface of the sensor 3000.

The sensor interface 3300 may indicate a part that connects the sensor 3000 and the wearable device 2000 when the sensor 3000 is attached to the wearable device 2000, and may function as a path on which the sensor 3000 and the wearable device 2000 exchange information.

The sensor interface 3300 may include a plurality of electrodes that may be electrically connected to the wearable device 2000. For example, the sensor interface 3300 may include a ground electrode, an electrode for sensing attachment or detachment of the sensor 3000, an electrode for checking a power supply to the sensor 3000, an electrode for transmitting data to the wearable device 2000, an electrode for receiving data from the wearable device 2000, a clock electrode for receiving an input of a clock signal, etc.

The sensor interface 3300 may be disposed on a front surface of the sensor 3000 on which the irradiator 3100 and the detector 3200 are disposed. Alternatively, the sensor interface 3300 may be disposed on a rear surface of the sensor 3000. For example, as illustrated in FIG. 6, the sensor interface 3300 may be disposed on the rear surface of the sensor 3000, which is the side opposite the front surface. Hereinafter, with reference to FIGS. 7 and 8, a second interface 2330 of the wearable device 2000 to which the chip-type sensor 3000 may be attached will be described.

Figure 7:
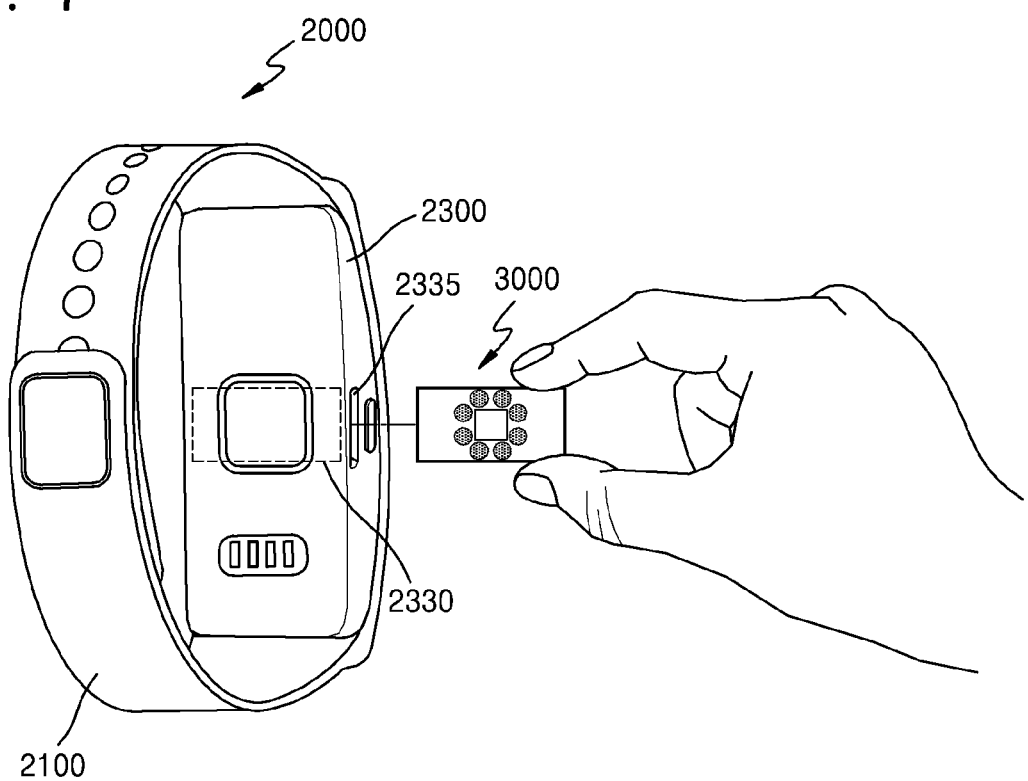
FIG. 7 illustrates a second interface of a wearable device, according to another exemplary embodiment.

FIG. 7 illustrates the second interface 2330 of the wearable device 2000, according to another exemplary embodiment.

Referring to FIG. 7, the wearable device 2000 may include the strap part 2100 that allows the wearable device 2000 to be worn on a body part of a user, and the main body 2300 that is connected to the strap part 2100. As illustrated in FIG. 7, the wearable device 2000 may be a watch-type wearable device but is not limited thereto and may have one of various forms including a necklace-type wearable device, a bracelet-type wearable device, a band-type wearable device, a hat-type wearable device, etc. The strap part 2100 and the main body 2300 may be separable or may have one body that is not separated.

As illustrated in FIG. 7, the second interface 2330 to which the sensor 3000 is attached may be disposed in the main body 2300 of the wearable device 2000.

The second interface 2330 may be disposed at a predetermined position of the main body 2300 that is connected to the strap part 2100. For example, the second interface 2330 may be disposed in the main body 2300. The second interface 2330 may receive biological signal detection information from the sensor 3000 that is attached to the wearable device 2000. Also, the second interface 2330 may receive a biological signal that is detected by the attached sensor 3000. Here, in a case of the photo-sensor such as the sensor 3000 shown in FIG. 6, the biological signal detection information may include information about a wavelength and intensity of light that is radiated by the sensor 3000 attached to the wearable device 2000.

As illustrated in FIG. 7, a position of the second interface 2330 with respect to the main body 2300 of the wearable device 2000 may be in the main body 2300. The sensor 3000 may be attached at the second interface 2330 in the main body 2300 of the wearable device 2000 via a slot 2335 formed in an exterior case of the main body 2300. Also, the second interface 2330 and the slot 2335 that corresponds to the second interface 2330 may simultaneously exist at several positions of the main body 2300.

Referring to FIG. 7, the sensor 3000 may be attached or detached even when the user wears the wearable device 2000. Also, when the sensor 3000 malfunctions or is broken, the user may detach the sensor 3000 from the wearable device 2000 and may repair only the sensor 3000.

As illustrated in FIG. 7, when the wearable device 2000 is a watch-type wearable device, a predetermined portion of the exterior case of the main body 2300 that contacts the body part of the user who wears the wearable device 2000 may be transparent. For example, in a case of the photo-sensor such as the sensor 3000 shown in FIG. 6, the photo-sensor may radiate light to the body part of the user so as to detect a biological signal. When the sensor 3000 is attached to the second interface 2330 in the main body 2300 of the wearable device 2000, the predetermined portion of the exterior case of the main body 2300 that corresponds to an radiation path of the light may be formed of a transparent material in order to allow the light to pass through the predetermined portion of the exterior case so as to irradiate the body part of the user.

In addition, the predetermined portion (e.g., a cover) of the exterior case of the main body 2300 may open or close according to whether the second interface 2330 is attached to the sensor 3000. For example, in a case where the photo-sensor such as the sensor 3000 of FIG. 6 is attached to the second interface 2330, the predetermined portion of the exterior case of the main body 2300 that corresponds to the radiation path of the light may open in order to allow the light to pass through the predetermined portion of the exterior case so as to irradiate the body part of the user. On the other hand, if the sensor 3000 is detached from the second interface 2330, the open portion may close.

Figure 8:
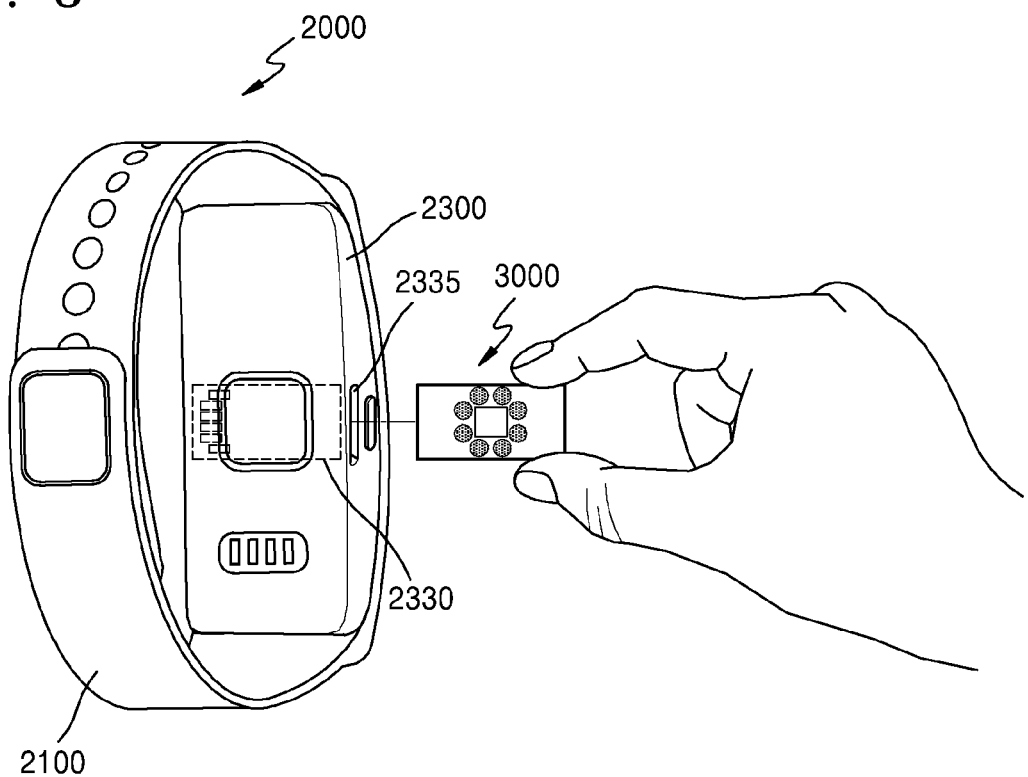
FIG. 8 illustrates an inside configuration of a main body in which the second interface of the wearable device is disposed, according to another exemplary embodiment.

FIG. 8 illustrates an inside of the main body 2300 in which the second interface 2330 of the wearable device 2000 is disposed, according to another exemplary embodiment.

Referring to FIG. 8, the second interface 2330 to which the sensor 3000 is attached is illustrated by using a dotted line, and pins of the second interface 2330 are also illustrated.

When the sensor 3000 is attached to the second interface 2330 of the wearable device 2000, the pins of the second interface 2330 may respectively contact electrodes of the sensor interface 3300 of the sensor 3000 and may connect the wearable device 2000 and the sensor 3000 so as to make data exchanged between the wearable device 2000 and the sensor 3000 that is attached to the wearable device 2000. The second interface 2330 may have the pins that may be electrically connected to the sensor 3000. For example, the second interface 2330 may have a pin for connection to a ground, a sensing pin for sensing attachment or detachment of the sensor 3000, a power pin for checking a power supply to the attached sensor 3000, a transmitting pin for transmitting data to the attached sensor 3000, a receiving pin for receiving data from the attached sensor 3000, a clock pin for receiving a clock signal, or the like.

Figure 9:
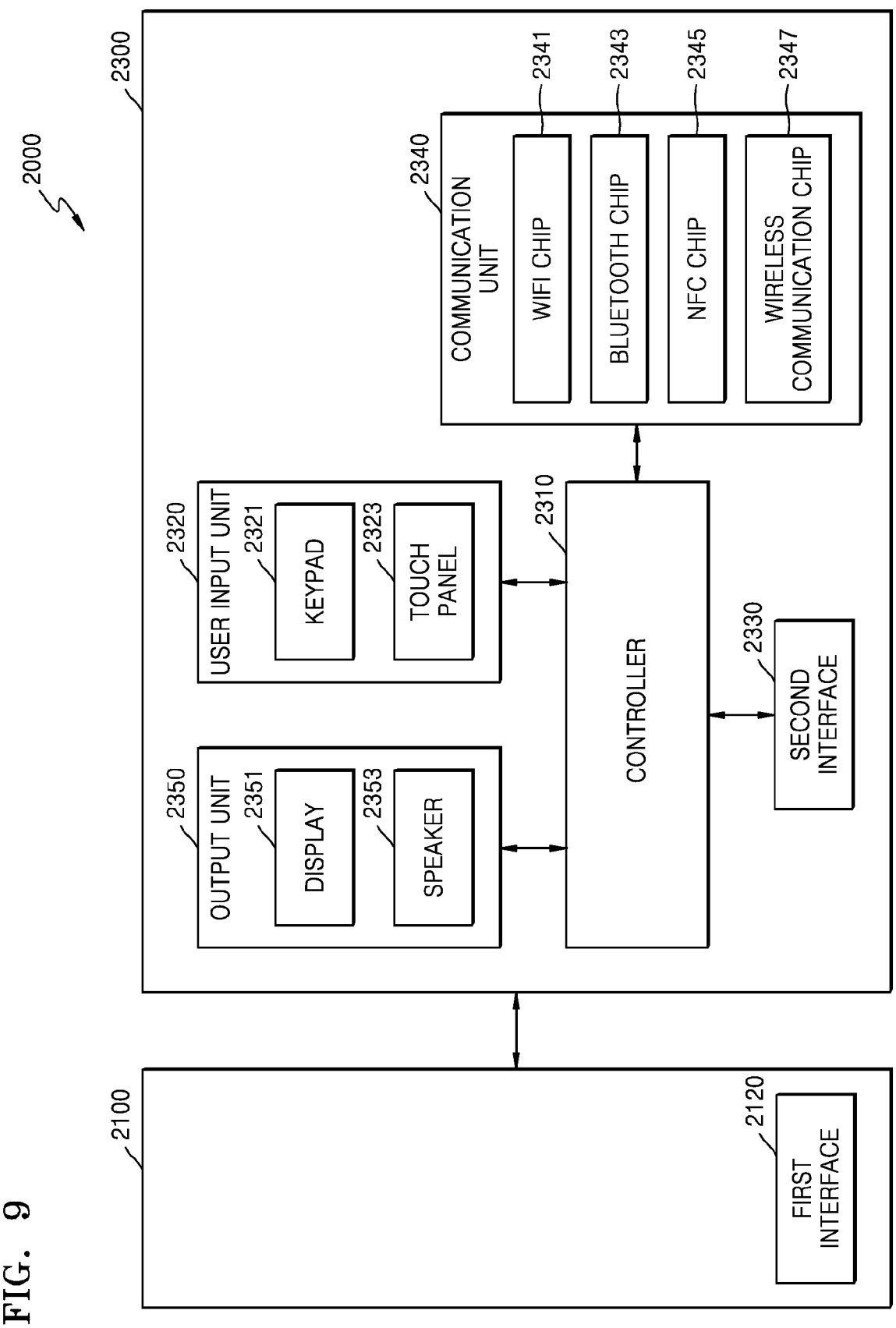
FIG. 9 is a block diagram illustrating a configuration of a wearable device, according to another exemplary embodiment.

FIG. 9 is a block diagram illustrating a configuration of the wearable device 2000, according to another exemplary embodiment. It is obvious to one of ordinary skill in the art that the wearable device 2000 may further include general-use elements as well as the elements shown in FIG. 9.

Referring to FIG. 9, the wearable device 2000 may include the strap part 2100 and the main body 2300. The strap part 2100 indicates a configuration of the wearable device 2000 that has a form to allow the wearable device 2000 to be worn on a body part of a user, and the main body 2300 indicates another configuration of the wearable device 2000 that performs a characteristic function of the wearable device 2000.

The user may attach or detach the sensor 3000 for detecting a biological signal to the wearable device 2000 or from the wearable device 2000. For example, the user may attach the sensor 3000 to detect one type of a biological signal, and then detach the attached sensor 3000 to replace the attached sensor 3000 with another sensor to detect another type of a biological signal. To do so, at least one interface that makes the sensor 3000 attachable to or detachable from the strap part 2100 or the main body 2300 may be arranged. For convenience of description, an interface that is disposed at the strap part 2100 may be referred to as the first interface 2120, and an interface that is disposed at the main body 2300 may be referred to as the second interface 2330. Here, according to a type of a detection-target biological signal, a type and form of the sensor 3000 may vary, and a position of the wearable device 2000 to which the sensor 3000 is to be attached may vary.

Referring to FIG. 9, the strap part 2100 of the wearable device 2000 may include the first interface 2120. In other words, the first interface 2120 may be disposed at a predetermined position of the strap part 2100 of the wearable device 2000. The first interface 2120 may receive biological signal detection information from the sensor 3000 that is attached to the wearable device 2000. Also, the first interface 2120 may receive a biological signal that is detected by the attached sensor 3000.

Detailed descriptions about the first interface 2120, which are the same as the aforementioned contents, will be omitted here, and the descriptions provided with reference to FIGS. 3 through 5 may be applied to the first interface 2120 of FIG. 9.

Referring to FIG. 9, the main body 2300 of the wearable device 2000 may include a controller 2310, a user input unit 2320, a second interface 2330, a communication unit 2340, and an output unit 2350.

The controller 2310 may include a random access memory (RAM), a read only memory (ROM), a central processing unit (CPU), and a graphic processing unit (GPU). The RAM, the ROM, the CPU, the GPU, or the like may be connected to each other via a data bus.

The CPU may access a memory and may perform a booting process by using an operating system (OS) stored in the memory. Then, the CPU may perform various operations by using various programs, contents, data, or the like stored in the memory.

The ROM may store an instruction set or the like for booting up a system. For example, when a turn on command is input to the wearable device 2000 and a power is supplied to the wearable device 2000, the CPU may copy the OS stored in the memory to the RAM according to the instruction set stored in the ROM, may execute the OS, and may boot up the system. When the booting process is complete, the CPU may copy the various programs stored in the memory to the RAM, may execute the programs copied to the RAM, and thus may perform various operations. When the booting process of the wearable device 2000 is complete, the GPU displays a user interface screen on a region of a display 2351. In more detail, the GPU may generate a screen on which an electronic document including various objects such as contents, icons, menu, or the like is displayed. The GPU calculates coordinates values by which the objects are displayed according to a layout of the screen, and calculates attribute values such as forms, sizes, or colors of the objects. Then, the GPU may generate screens having various layouts that include the objects, based on the calculated attribute values. The screens that are generated by the GPU may be provided to the display 2351 and may be displayed on regions of the display 2351, respectively.

The user input unit 2320 may receive inputs of various commands from a user. The user input unit 2320 may include at least one of a keypad 2321 and a touch panel 2323.

The keypad 2321 may include various types of keys such as at least one mechanical button, a wheel, etc. that are formed in various regions such as a front part, a side part, or a rear part of the main body 2300 of the wearable device 2000.

The touch panel 2323 may sense a touch input by a user and may output a value of a touch event that corresponds to the sensed touch input. The touch panel 2323 may be combined with a display panel and thus may be formed as a touchscreen. The touchscreen may be configured as a capacitive touchscreen or a resistive touchscreen by using various types of touch sensors. The capacitive touchscreen may calculate touch coordinates by sensing a small amount of electricity generated when a body part of the user touches the surface of the capacitive touchscreen, which is coated with a dielectric. The resistive touchscreen may include two embedded electrode plates and may calculate touch coordinates by sensing a flow of current that occurs when the user touches the resistive touchscreen and thus upper and lower plates of a touched point contact each other. The touch event that occurs on the touchscreen may be mainly generated by a finger of a person but may also be generated by an object formed of a conductive material capable of changing capacitance.

The second interface 2330 may be disposed at a predetermined position of the main body 2300 that is connected to the wearable device 2000. For example, the second interface 2330 may be disposed in the main body 2300. The second interface 2330 may receive biological signal detection information from the sensor 3000 that is attached to the wearable device 2000. Also, the second interface 2330 may receive a biological signal that is detected by the attached sensor 3000.

Detailed descriptions about the second interface 2330, which are the same as the aforementioned contents, will be omitted here, and the descriptions provided with reference to FIGS. 7 and 8 may be changelessly applied to the second interface 2330 of FIG. 9.

The communication unit 2340 may communicate with various types of external devices according to various communication ways. The communication unit 2340 may include at least one selected from a WiFi chip 2341, a Bluetooth chip 2343, a near field communication (NFC) chip 2345, and a wireless communication chip 2347. The controller 2310 may communicate with various external devices by using the communication unit 2340.

The WiFi chip 2341 and the Bluetooth chip 2343 may communicate with another device by using WiFi and Bluetooth, respectively. If the WiFi chip 2341 or the Bluetooth chip 2343 is used, the WiFi chip 2341 or the Bluetooth chip 2343 may first transmit and receive various types of connection information including a service set identification (SSID), a session key, or the like, may connection communication by using the connection information, and then may transmit and receive various types of information. The NFC chip 2345 indicates a chip that operates in an NFC way by using a 13.56 MHz band from among various radio frequency-identification (RF-ID) frequency bands such as 135 kHz, 13.56 MHz, 433 MHz, 860-960 MHz, 2.45 GHz, or the like. The wireless communication chip 2347 indicates a chip that communicates with another device according to various communication standards such as the Institute of Electrical and Electronics Engineers (IEEE), ZigBee, $3^{rd}$ generation (3G), $3^{rd}$ Generation Partnership Project (3GPP), Long Term Evolution (LTE), or the like.

The output unit 2350 may include the display 2351 and a speaker 2353.

The display 2351 may include a display panel and a controller for controlling the display panel. The display panel may be embodied as various displays including a liquid crystal display (LCD), an organic light-emitting diode (OLED) display, an active-matrix organic light-emitting diode (AM-OLED) display, a plasma display panel (PDP), or the like. The display 2351 may be combined with the touch panel 2323 of the user input unit 2320 and thus may be provided as a touchscreen. For example, the touchscreen may include an integrated module formed by stacking the display panel and the touch panel 2323.

The speaker 2353 may output audio data that is generated by an audio processor.

Names of the elements of the wearable device 2000 may be changed. Also, not all elements shown in FIG. 9 are necessary elements. That is, the wearable device 2000 may be embodied with more or less elements than the elements shown in FIG. 9.

The wearable device 2000 may exchange, by using at least one of the elements, information with the sensor 3000 that is attached to the wearable device 2000 and may perform operations below.

An interface of the wearable device 2000 that includes at least one of the first interface 2120 and the second interface 2330 may receive biological signal detection information and a biological signal detected by the sensor 3000, from the sensor 3000 that is attached to the wearable device 2000. The biological signal detection information and the biological signal that is detected by the attached sensor 3000 may be sequentially or simultaneously received via the interface of the wearable device 2000.

The controller 2310 of the wearable device 2000 may recognize a type of the attached sensor 3000, based on the biological signal detection information that is received via the interface. For example, if the sensor 3000 attached to the wearable device 2000 is a photo-sensor that radiates light and detects the biological signal, the biological signal detection information may include information about a wavelength and intensity of light that is radiated by the sensor 3000. Here, according to a degree of the wavelength and intensity of the light, the wearable device 2000 may further exactly recognize a type of the biological signal that is detected by the photo-sensor.

The interface of the wearable device 2000 that includes at least one of the first interface 2120 and the second interface 2330 may include a plurality of sub-interfaces to which the sensors 3000 may be attached. The controller 2310 of the wearable device 2000 may recognize types of one or more sensors 3000 that are attached to the plurality of sub-interfaces.

Also, the controller 2310 of the wearable device 2000 may generate biological information that corresponds to the recognized type of the sensor 3000, based on the biological signal that is received via the interface of the wearable device 2000 that includes at least one of the first interface 2120 and the second interface 2330. The interface of the wearable device 2000 may receive all detected biological signals or only a user-desired biological signal from the one or more attached sensors 3000. For example, the output unit 2350 in the form of a touchscreen may display, on a user interface of the wearable device 2000, one or more functions of the sensor 3000 that is recognized by the controller 2310, and may receive an input of selecting a user-desired function from among the one or more displayed functions of the sensor 3000. The interface of the wearable device 2000 may receive, from the attached sensor 3000, a biological signal that corresponds to the selected function.

The output unit 2350 of the wearable device 2000 may output the biological information that is generated based on the biological signal that is received from the sensor 3000 attached to the wearable device 2000. Here, if the interface of the wearable device 2000 receives all biological signals that are detected by the sensor 3000 attached to the wearable device 2000, the output unit 2350 of the wearable device 2000 may output all biological information or only user-desired biological information. For example, the output unit 2350 in the form of the touchscreen may display, on the user interface of the wearable device 2000, one or more functions of the sensor 3000 that is recognized by the controller 2310, and may receive an input of selecting a user-desired function from among the one or more displayed functions of the sensor 3000. The output unit 2350 of the wearable device 2000 may output biological information that corresponds to the selected function.

The output unit 2350 of the wearable device 2000 may output information about changes in biological information during a predetermined period set by the user. In other words, the wearable device 2000 may store a plurality of pieces of biological information that were generated during the predetermined period, and if the user requests an output of the plurality of pieces of biological information during the predetermined period, the wearable device 2000 may output the information about the changes in the biological information by simultaneously outputting the plurality of pieces of biological information during the predetermined period in a time-sequential order.

Figure 10:
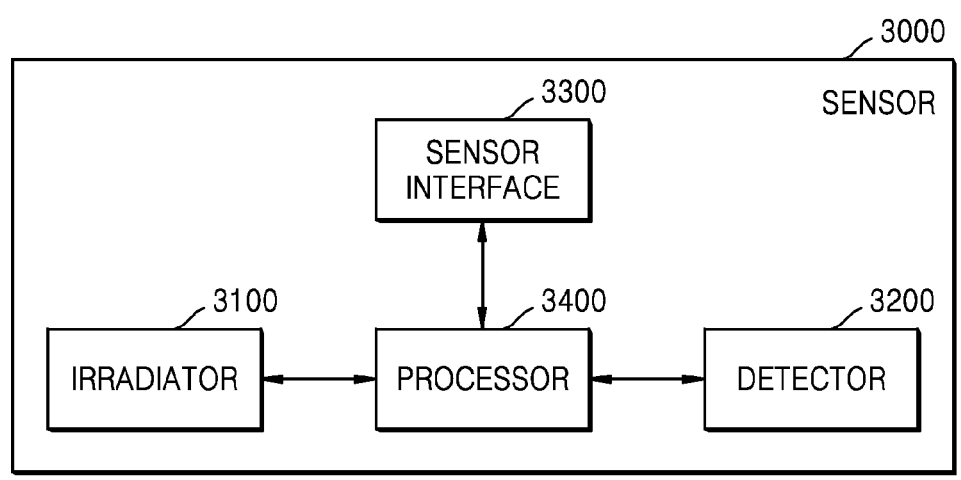
FIG. 10 is a block diagram illustrating a configuration of a sensor that is attachable to or detachable from a wearable device, according to another exemplary embodiment.

FIG. 10 is a block diagram illustrating a configuration of the sensor 3000 that is attachable to or detachable from the wearable device 2000, according to another exemplary embodiment. It is obvious to one of ordinary skill in the art that the sensor 3000 may further include general-use elements as well as the elements shown in FIG. 10.

Detailed descriptions about the sensor 3000 that is attachable to or detachable from the wearable device 2000, which are the same as the aforementioned contents, will be omitted here, and the descriptions provided with reference to FIGS. 2 and 6 may be changelessly applied to the sensor 3000 of FIG. 10.

Referring to FIG. 10, the sensor 3000 that is attachable to or detachable from the wearable device 2000 may include the irradiator 3100, the detector 3200, the sensor interface 3300, and a processor 3400. A form or a configuration of the 3000 that is attachable to or detachable from the wearable device 2000 may vary according to a method of detecting a biological signal. Alternatively, a type of the sensor 3000 may vary according to a detection-target biological signal, or one sensor 3000 may detect various biological signals.

The sensor 3000 that is attachable to or detachable from the wearable device 2000 may automatically operate when the sensor 3000 is attached to the wearable device 2000 and a power is supplied to the sensor 3000, or may operate according to setting or manual manipulation by a user.

The irradiator 3100 may radiate light or a wavelength to a body part of the user to detect a biological signal. If the sensor 3000 of FIG. 2 is a photo-sensor, the irradiator 3100 may correspond to an irradiation part that radiates light.

The detector 3200 may detect the biological signal that is generated in response to the light or the wavelength being radiated by the irradiator 3100 onto the body part and then being reflected off the body part towards the detector 2. Thus, a form and a detecting method of the detector 3200 may vary according to a form and an irradiating method of the irradiator 3100.

The sensor interface 3300 may correspond to a part that connects the sensor 3000 and the wearable device 2000 when the sensor 3000 is attached to the wearable device 2000, and may contact an interface of the wearable device 2000 that includes at least one of the first interface 2120 and the second interface 2330. The sensor interface 3300 may function as a path on which the sensor 3000 and the wearable device 2000 exchange information. The sensor 3000 that is attached to the wearable device 2000 may transmit, to the wearable device 2000, biological signal detection information and a biological signal that is detected by the attached sensor 3000.

The processor 3400 may control general operations of the sensor 3000. For example, when the sensor 3000 is attached to the wearable device 2000 and thus the sensor interface 3300 contacts the first interface 2120 or the second interface 2330 of the wearable device 2000, the processor 3400 may control at least one of the irradiator 3100, the detector 3200, and the sensor interface 3300 so as to make the sensor 3000 exchange information with the wearable device 2000.

Figure 11:
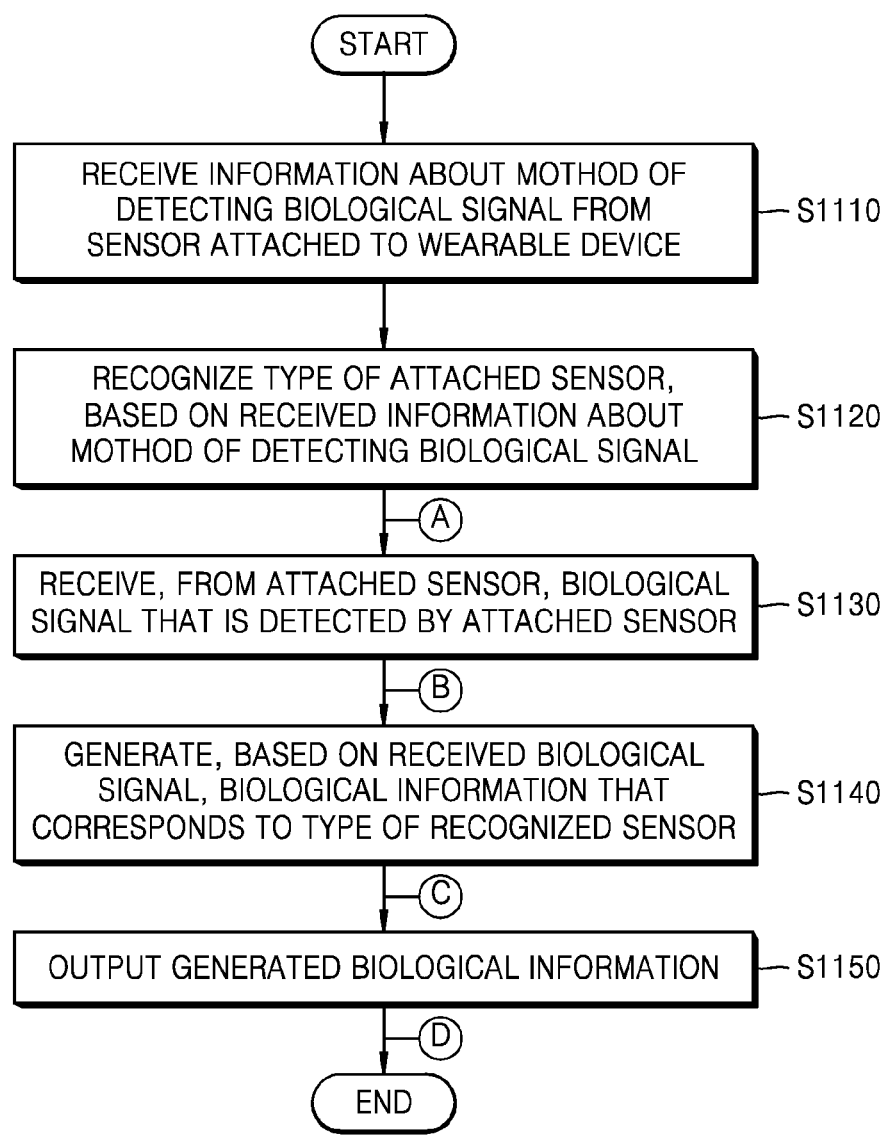
FIG. 11 is a flowchart of a method of controlling a wearable device, according to an exemplary embodiment.

FIG. 11 is a flowchart of a method of controlling the wearable device 2000, according to an exemplary embodiment. Hereinafter, although descriptions are omitted, if the descriptions are described above with respect to the wearable device 2000 and the sensor 3000 that is attachable to or detachable from the wearable device 2000, the descriptions may also be applied to the method of controlling the wearable device 2000.

The wearable device 2000 may receive biological signal detection information from the sensor 3000 that is attached to the wearable device 2000 (operation S1110). If a plurality of the sensors 3000 are attached to the wearable device 2000, the wearable device 2000 may receive a plurality of pieces of biological signal detection information from the plurality of the sensors 3000. Here, the plurality of the sensors 3000 that are attached to the wearable device 2000 may be same-type sensors or different-type sensors.

The wearable device 2000 may recognize a type of the sensor 3000 attached to the wearable device 2000, based on the biological signal detection information that is received from the sensor 3000 (operation S1120). For example, if the sensor 3000 that is attached to the wearable device 2000 is a photo-sensor, the biological signal detection information may include information about a wavelength and intensity of light that is radiated by the attached sensor 3000. Here, according to a degree of the wavelength and intensity of the light, the wearable device 2000 may further exactly recognize a type of the biological signal that is detected by the photo-sensor.

The wearable device 2000 may receive, from the sensor 3000, the biological signal that is detected by the sensor 3000 attached to the wearable device 2000 (operation S1130). The wearable device 2000 may receive all biological signals that are detected by the plurality of the attached sensors 3000. Alternatively, the wearable device 2000 may receive a biological signal that corresponds to a user-desired function. Hereinafter, with reference to FIG. 12, this will be described in detail.

Figure 12:
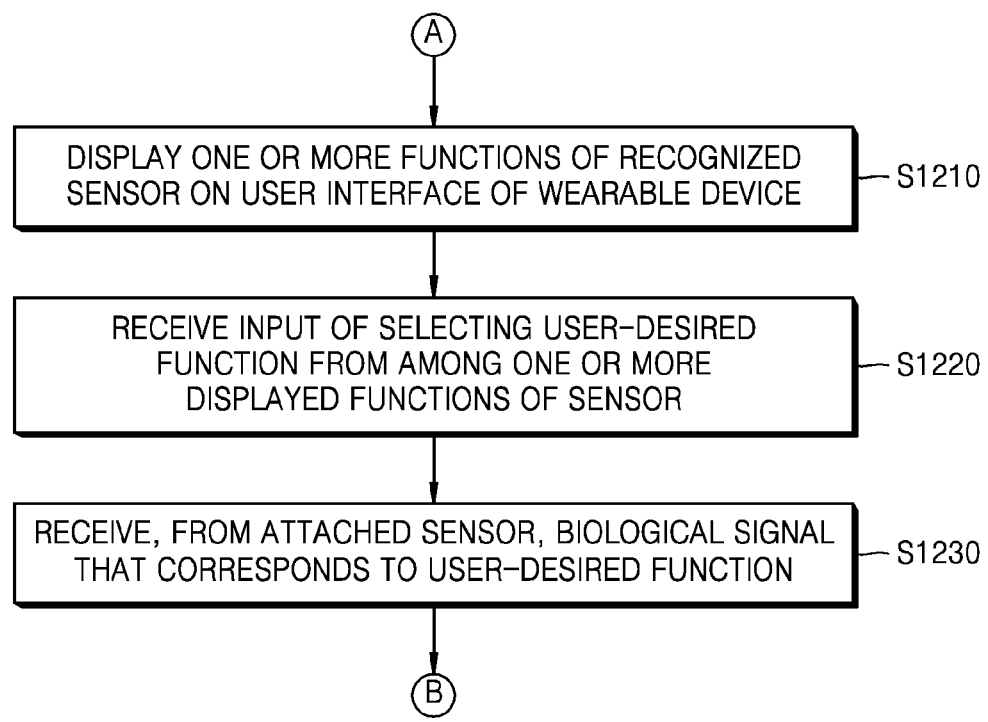
FIG. 12 is a flowchart particularly illustrating an operation of receiving a biological signal in the method of controlling the wearable device.

FIG. 12 is a flowchart particularly illustrating an operation of receiving a biological signal in the method of controlling the wearable device 2000.

The wearable device 2000 may display one or more functions of the recognized sensor 3000 on a user interface of the wearable device 2000 (operation S1210).

The wearable device 2000 may receive an input of selecting a user-desired function from among the one or more functions of the recognized sensor 3000 that are displayed on the user interface (operation S1220). One sensor 3000 may have several functions related to detecting a biological signal or a plurality of the sensors 3000 may be attached to the wearable device 2000. Thus, a user may select at least one of the functions.

The wearable device 2000 may receive a biological signal that corresponds to the user-desired function, from the sensor 3000 that is attached to the wearable device 2000 (operation S1230). For example, after the user selects the user-desired function of the sensor 3000, the sensor 3000 that is attached to the wearable device 2000 may detect the biological signal that corresponds to the user-desired function and may transmit the biological signal to the wearable device 2000. Further, the sensor 3000 may detect one or more types of biological signals, and if the user-desired function of the sensor 3000 is input, the sensor 3000 may transmit, to the wearable device 2000, only the biological signal that corresponds to the user-desired function.

Referring back to FIG. 11, the wearable device 2000 may generate, based on the received biological signal, biological information that corresponds to a type of the recognized sensor 3000 (operation S1140). Here, the wearable device 2000 may generate all of the received biological signals into biological information that is recognizable by the user or may generate only some of the received biological signals into biological information. For example, if the sensor 3000 that is attached to the wearable device 2000 transmits all biological signals that are detected by the sensor 3000, the wearable device 2000 may receive all the biological signals and may generate only some of the biological signals into biological information that is recognizable by the user, according to setting or manual manipulation by the user.

Figure 13:
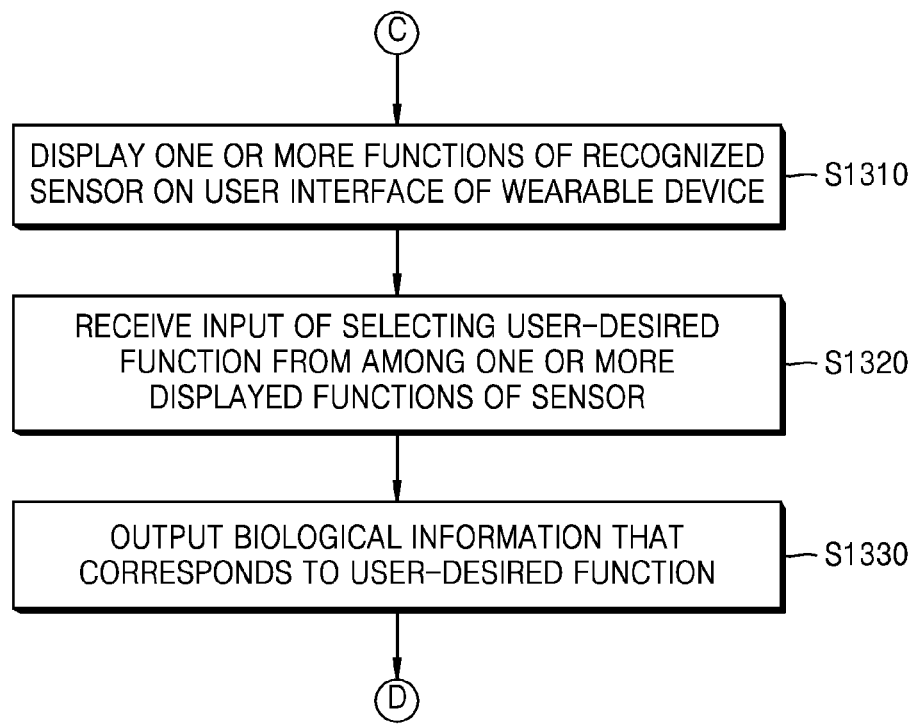
FIG. 13 is a flowchart particularly illustrating an operation of outputting biological information in the method of controlling the wearable device.

The wearable device 2000 may output the generated biological information (operation S1150). Here, the wearable device 2000 may output information about changes in the biological information over time during a predetermined period. The predetermined period may be set by the user. The wearable device 2000 may output all of generated biological information. Alternatively, the wearable device 2000 may output biological information that corresponds to the user-desired function. Hereinafter, with reference to FIG. 13, this is described in detail.

The wearable device 2000 may display, on a user interface of the wearable device 2000, one or more functions of the sensor 3000 that is recognized by the wearable device 2000 (operation S1310).

The wearable device 2000 may receive an input of selecting a user-desired function from among the one or more functions of the sensor 3000 that are displayed on the user interface (operation S1320).

The wearable device 2000 may output biological information that corresponds to the user-desired function (operation S1330).

As described above, according to the one or more of the above exemplary embodiments, a user may easily attach or detach a sensor while the user wears the wearable device, thus, if a sensor has broken or a different sensor is required, the user may easily change the sensor.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A wearable device comprising:
    an interface configured to receive, from a sensor that is detachably attached to the wearable device, a biological signal detected by the sensor and information about a method of detecting the biological signal; and
    a controller configured to recognize a type of the sensor based on the information about the method of detecting the biological signal, and generate biological information corresponding to the recognized type of the sensor, based on the biological signal,
    wherein the information about the method of detecting the biological signal comprises information about a wavelength and an intensity of light that is radiated by the sensor, and the controller is further configured to recognize the type of the sensor based on a value of the wavelength and a degree of the intensity of light that is radiated by the sensor.

2. The wearable device of claim 1, further comprising an output unit configured to output the biological information, display one or more functions of the sensor on a user interface of the wearable device, and receive an input of selecting a user-desired function from among the one or more functions, and wherein the interface is further configured to receive, from the sensor, a biological signal that corresponds to the user-desired function.

3. The wearable device of claim 1, further comprising an output unit configured to display one or more functions of the sensor on a user interface of the wearable device, receive an input for selecting a user-desired function from among the one or more functions, and output biological information that corresponds to the user-desired function.

4. The wearable device of claim 1, further comprising an output unit configured to output the biological information and output information about changes in the biological information over time during a predetermined period.

5. The wearable device of claim 1, wherein the interface comprises a plurality of sub-interfaces to which a plurality of sensors of different types are detachably attached, the plurality of sensors comprising the sensor, and
the controller is further configured to recognize at least one sensor from among the plurality of sensors.

6. A method of a wearable device comprising:
receiving, from a sensor that is detachably attached to the wearable device, information about a method of detecting a biological signal;
recognizing a type of the sensor, based on the information about the method of detecting the biological signal;
receiving, from the sensor, the biological signal detected by the sensor; and
generating, based on the biological signal, biological information that corresponds to the recognized type of the sensor,
wherein the information about the method of detecting the biological signal comprises information about a wavelength and an intensity of light that is radiated by the sensor, and the recognizing comprises recognizing the type of the sensor based on a value of the wavelength and a degree of the intensity of light that is radiated by the sensor.

7. The method of claim 6, wherein the receiving the biological signal comprises:
displaying one or more functions of the sensor on a user interface of the wearable device;
receiving an input of selecting a user-desired function from among the one or more functions; and
receiving, from the sensor, a biological signal that corresponds to the user-desired function.

8. The method of claim 6, further comprising:
displaying one or more functions of the sensor on a user interface of the wearable device;
receiving an input for selecting a user-desired function from among the one or more functions; and
outputting biological information that corresponds to the user-desired function.

9. The method of claim 6, further comprising:
outputting the biological information; and
outputting information about changes in the biological information over time during a predetermined period.

10. The method of claim 6, wherein the receiving the information about the method of detecting the biological signal comprises receiving the information about the method of detecting the biological signal from each of different-type sensors that are attached to the wearable device, the different-type sensors comprising the sensor.

11. The wearable device of claim 1, wherein the interface is further configured to receive, from the sensor, biological signals of different types, and
wherein the controller is further configured to recognize a type of each of the biological signals based on the value of the wavelength and the degree of the intensity of light that is radiated by the sensor corresponding to each of the biological signals.

12. The wearable device of claim 1, wherein the interface comprises a plurality of sub-interfaces to which a plurality of sensors are detachably attached, the plurality of sensors configured to detect biological signals of different types, and a position of a sub-interface to which each sensor of the plurality of sensors is detachably attached is varied according to a type of a biological signal to be measured by each sensor.

13. A wearable device comprising:
an interface configured to receive, from a sensor that is detachably attached to the wearable device, a biological signal detected by the sensor and information about a method of detecting the biological signal; and
a controller configured to recognize a type of the sensor based on the information about the method of detecting the biological signal, and generate biological information corresponding to the recognized type of the sensor, based on the biological signal,
wherein the interface comprises a plurality of sub-interfaces to which a plurality of sensors of different types are detachably attached, the plurality of sensors comprising the sensor, and
wherein the information about the method of detecting the biological signal comprises information about a wavelength and an intensity of light that is radiated by the sensor, and the controller is further configured to recognize a type of each sensor of the plurality of sensors based on a value of the wavelength and a degree of the intensity of light that is radiated by each sensor.

* * * * *